(12) United States Patent
Kurrus et al.

(10) Patent No.: US 8,518,064 B2
(45) Date of Patent: Aug. 27, 2013

(54) METHOD FOR ANCHORING OCCLUSION PLUG

(75) Inventors: Michael R. Kurrus, Ellettsville, IN (US); Grant T. Hoffman, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 743 days.

(21) Appl. No.: 12/641,021

(22) Filed: Dec. 17, 2009

(65) Prior Publication Data

US 2011/0152902 A1   Jun. 23, 2011

(51) Int. Cl.
*A61B 17/08* (2006.01)

(52) U.S. Cl.
USPC .......................................................... 606/158

(58) Field of Classification Search
USPC .................. 606/158, 155, 213, 194, 232
See application file for complete search history.

(56) References Cited

U.S. PATENT DOCUMENTS

| | | | |
|---|---|---|---|
| 4,228,056 A | 10/1980 | Stoy | |
| 4,578,061 A | 3/1986 | Lemelson | |
| 4,663,358 A | 5/1987 | Hyon et al. | |
| 4,675,361 A | 6/1987 | Ward, Jr. | |
| 5,190,528 A | 3/1993 | Fonger et al. | |
| 5,258,042 A | 11/1993 | Mehta | |
| 5,275,616 A * | 1/1994 | Fowler ......................... | 606/213 |
| 5,354,279 A | 10/1994 | Hofling | |
| 5,456,693 A | 10/1995 | Conston et al. | |
| 5,464,395 A | 11/1995 | Faxon et al. | |
| 5,570,585 A | 11/1996 | Vaynberg | |
| 5,718,237 A | 2/1998 | Haaga | |
| 5,823,198 A | 10/1998 | Jones et al. | |
| 6,206,931 B1 | 3/2001 | Cook et al. | |
| 6,217,554 B1 | 4/2001 | Green | |
| 6,238,403 B1 | 5/2001 | Greene, Jr. et al. | |
| 6,245,090 B1 | 6/2001 | Gilson et al. | |
| 6,375,989 B1 | 4/2002 | Badylak et al. | |
| 6,491,707 B2 * | 12/2002 | Makower et al. ............. | 606/157 |
| 6,602,241 B2 | 8/2003 | Makower et al. | |
| 6,602,261 B2 | 8/2003 | Greene, Jr. et al. | |
| 6,749,598 B1 * | 6/2004 | Keren et al. ................... | 604/508 |
| 6,818,018 B1 | 11/2004 | Sawhney | |
| 6,860,867 B2 | 3/2005 | Seward et al. | |
| 6,939,377 B2 | 9/2005 | Jayaraman et al. | |
| 2003/0109899 A1 | 6/2003 | Fisher et al. | |

(Continued)

*Primary Examiner* — Corrine M McDermott
*Assistant Examiner* — Christina Lauer
(74) *Attorney, Agent, or Firm* — Brinks Hofer Gilson & Lione

(57) ABSTRACT

A method for occluding a body vessel in a patient to block or reduce blood flow therethrough includes puncturing a blood vessel wall at a proximal vessel entry site with a hollow needle and extending the needle through the proximal entry site into the vessel lumen. The needle is extended through the vessel lumen and extended through the vessel wall at a distal vessel exit site into the extravascular space surrounding the distal vessel exit site. An expandable biocompatible material, such as expandable extracellular matrix (ECM) material, is then ejected though the distal end of the needle into the extravascular space. Then, while continuing to eject the expandable biocompatible plug material, the distal end of the needle is retracted back through the distal vessel exit site into the vessel lumen, such that the plug material continuously extends between the extravascular space surrounding the distal vessel exit site into the vessel lumen. When the plug material is delivered into the lumen of the vessel, the plug material expands, anchoring the plug material to the vessel wall, whereby the plug material forms an occluding plug in the vessel lumen blocking or reducing blood flow therethrough.

15 Claims, 1 Drawing Sheet

(56) References Cited

U.S. PATENT DOCUMENTS

| | | |
|---|---|---|
| 2003/0206860 A1 | 11/2003 | Bleyer et al. |
| 2005/0085885 A1 | 4/2005 | Janke et al. |
| 2006/0008419 A1 | 1/2006 | Hissink et al. |
| 2006/0052816 A1 | 3/2006 | Bates et al. |
| 2006/0052822 A1* | 3/2006 | Mirizzi et al. ............ 606/214 |
| 2007/0166345 A1 | 7/2007 | Pavcnik et al. |
| 2007/0292472 A1 | 12/2007 | Paul et al. |
| 2009/0317469 A1 | 12/2009 | Johnson et al. |
| 2009/0318934 A1 | 12/2009 | Johnson et al. |
| 2009/0326577 A1* | 12/2009 | Johnson et al. ............ 606/213 |

\* cited by examiner

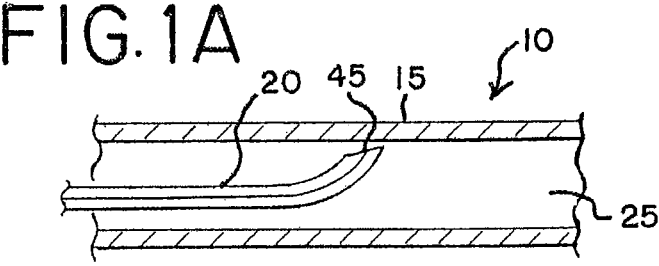
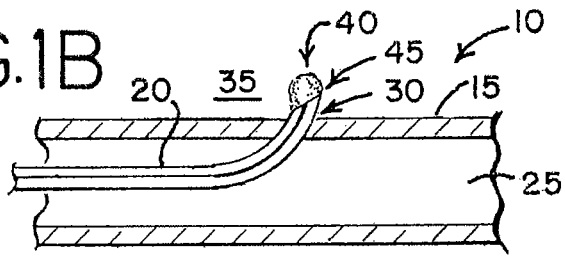
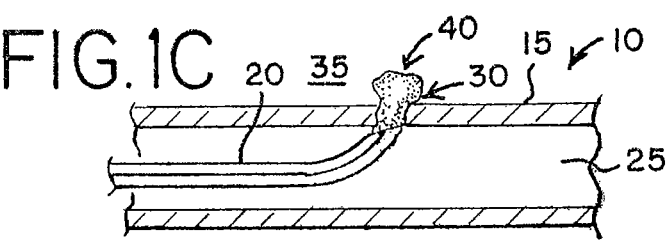
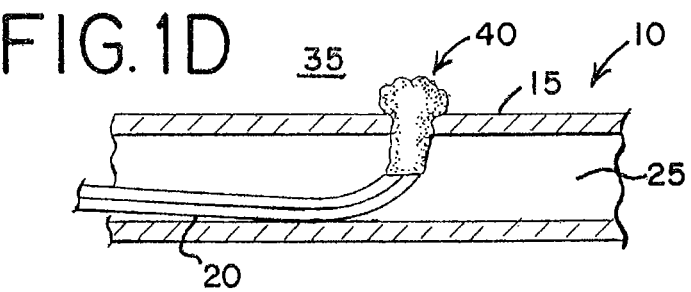
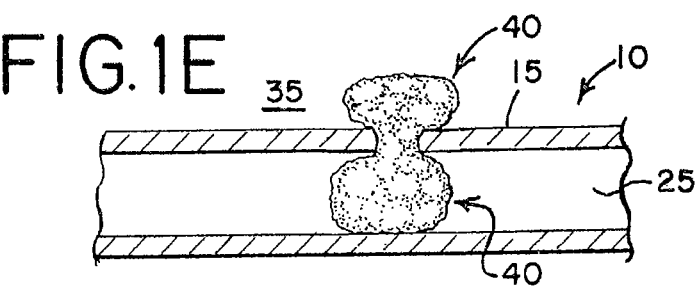

METHOD FOR ANCHORING OCCLUSION PLUG

TECHNICAL FIELD

This invention relates generally to a method for anchoring an expandable biocompatible plug material to a vessel wall to form an anchored occluding plug blocking or reducing blood flow to a desired vessel target, such as an artery supplying blood to a neoplastic tissue or tumor.

BACKGROUND

Occlusion of blood vessels is desired in a number of clinical situations. For example, vascular embolization has been used to control vascular bleeding, to occlude the blood supply to tumors, and to occlude vascular aneurysms, particularly intracranial aneurysms. For example, vascular embolization may be used to occlude or close off the vessels that are supplying blood to a tumor, especially when the tumor is difficult or impossible to remove. Following embolization, a tumor may shrink or it may continue to grow but more slowly, making chemotherapy or surgery a more effective option.

Embolization procedures may utilize a variety of embolic agents, including coils, foams, glues, or ethanol. Embolization coils are typically made of stainless steel and/or platinum, often in conjunction with vascular obstruction devices, including "spider" devices to prevent dislodgment of embolization coils beyond the site of delivery. A problem with these devices is that it takes time to occlude the vessel and often leaves beyond foreign, stainless steel materials in the body. Also, this arrangement is more complex because it may require the delivery of two separate devices to the vasculature. Another approach involves the direct injection of liquid, semi-solid, or solid occlusion agents, including sponge-like or foam plugs into target vessel sites. However, the performance of these agents and other related approaches suffer from problems of migration and difficulties of retrievability, when necessary.

Accordingly, there exists a need for improved vascular plug devices that can rapidly occlude a body vessel and become anchored thereto and that can promote cellular ingrowth and permanently integrate into the body tissues.

SUMMARY

In one aspect, a method for occluding a body vessel (such as an artery, vein, or duct) in a patient to block or reduce flow of bodily fluids therethrough includes puncturing a body vessel wall at a proximal vessel entry site with a hollow needle and extending the needle through the proximal entry site into the vessel lumen. The needle is extended through the vessel lumen and extended through the vessel wall at a distal vessel exit site into the extravascular space surrounding the distal vessel exit site. An expandable biocompatible material is then ejected though the distal end of the needle into the extravascular space. Then, while continuing to eject the expandable biocompatible plug material, the distal end of the needle is retracted back through the distal vessel exit site into the vessel lumen, such that the plug material continuously extends between the extravascular space surrounding the distal vessel exit site into the vessel lumen. When the plug material is delivered into the lumen of the vessel, the plug material expands, anchoring the plug material to the vessel wall, whereby the plug material forms an occluding plug in the vessel lumen blocking or reducing blood flow therethrough.

In another aspect, a method for occluding an artery in a patient to block or reduce blood flow to a neoplastic tissue or tumor includes puncturing an artery wall in an artery at a proximal artery entry site with a hollow needle, and extending the needle through the proximal entry site into the artery lumen. The needle is extended through the artery lumen and extended through the artery wall at a distal artery exit site into the extraarterial space surrounding the distal artery exit site. An expandable biocompatible material is then ejected though the distal end of the needle into the extraarterial space. Then, while continuing to eject the expandable biocompatible plug material, the distal end of the needle is retracted back through the distal artery exit site into the artery lumen, such that the plug material continuously extends between the extraarterial space surrounding the distal artery exit site into the artery lumen. When the plug material is delivered into the lumen of the artery, the plug material expands, anchoring the plug material to the artery wall, whereby the plug material forms an occluding plug in the artery lumen blocking or reducing blood flow therethrough.

The expandable biocompatible plug material may be configured as a solid plug, semi-gel composition, or flowable composition configured for passage through a hollow needle so as to expand and become anchored to the vessel or artery following release. The expandable biocompatible plug material may be formed from expandable sponge-like materials, expandable foam materials, expandable extracellular matrix (ECM) materials, expandable polymeric materials, expandable hydrogel materials, or combinations thereof.

In a desired embodiment, the expandable biocompatible plug material includes expandable ECM plug material. More particularly, the expandable ECM plug material may be formed by treating an ECM tissue source material with a sufficient quantity of alkaline medium for a sufficient period of time to produce an ECM material expandable in an aqueous fluid environment by a factor of at least 2-fold, up to about 6-fold or more.

BRIEF DESCRIPTION OF THE DRAWINGS

FIG. 1A illustrates an exemplary plan view of a needle extending though a vessel, such as an artery, following puncture through a proximal entry site.

FIG. 1B illustrates a plan view of the needle in FIG. 1A puncturing an arterial wall at a distal arterial exit site and releasing an expandable biocompatible plug material into the extraarterial space surrounding the distal arterial exit site.

FIG. 1C illustrates a plan view of the needle in FIG. 1B releasing the expandable plug material, while being retracted back into the artery lumen as the plug material begins to expand into the extraarterial space.

FIG. 1D illustrates a plan view of the needle releasing the expandable plug material into the artery lumen as the plug material continues to expand in the extraarterial space and becomes anchored to the arterial wall at the distal arterial exit site.

FIG. 1E illustrates a plan view of the plug material expandable in the extraarterial space and in the arterial lumen, and anchored to the arterial wall at the distal arterial exit site.

DETAILED DESCRIPTION

In order to provide a clear and consistent understanding of the specification and claims, the following definitions are provided.

As used herein, the term "proximal" is used in its conventional sense to refer to the end of the member (or component) that is closest to the operator during use.

The term "distal" is used in its conventional sense to refer to the end of the member (or component) that is initially inserted into the patient, or that is closest to the patient.

The term "expandable ECM material" refers to a porous ECM material composition obtained from a non-expandable ECM material treated under conditions that expand the volume of the non-expandable ECM material.

The terms "non-expandable ECM material" and "non-expandable tissue source" are used interchangeably to refer to a material composition processed from a natural ECM tissue source material, which has not been exposed to alkaline conditions, acid conditions or other conditions sufficient to substantially disrupt the collagen packing characteristics of the native ECM source material so as to increase its volume.

The term "biocompatible" refers to a material that is substantially non-toxic in the in vivo environment of its intended use, and that is not substantially rejected by the patient's physiological system or is non-antigenic. This can be gauged by the ability of a material to pass the biocompatibility tests set forth in International Standards Organization (ISO) Standard No. 10993; the U.S. Pharmacopeia (USP) 23; or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity, immunogenicity, and combinations thereof. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

FIGS. 1A-1E illustrate an exemplary method for occluding a blood vessel using an anchored plug material according to the present invention, such as occlusion of an artery in a patient for blocking or reducing blood flow to a neoplastic tissue or tumor. First, the wall of a vessel, such as an artery wall 15 in an artery 10 is penetrated at a proximal artery entry site (not shown) with a hollow needle 20. The needle 20 is then extended in a proximal to distal direction from the proximal entry site into the arterial lumen 25 (FIG. 1A). The needle 20 is then extended through the artery lumen 25 to a desired occlusion site, whereupon the distal end 45 of the needle 20 is penetrated through the artery wall 15 at a distal artery exit site 30 and into the extraarterial space 35 surrounding the distal artery exit site 30 (FIG. 1B). An expandable biocompatible plug material 40 is then ejected though the distal end 45 of the needle 20 into the extraarterial space (FIG. 1B). Then, while continuing to eject the expandable biocompatible plug material 40, the distal end 45 of the needle 20 is retracted back through the distal artery exit site 30 into the artery lumen 25, such that the plug material 40 continuously extends from the extraarterial space 35 surrounding the distal artery exit site 30, through the arterial wall 15, and into the artery lumen 25 (FIGS. 1C-1D). When the plug material 40 is delivered into the lumen of the artery, the plug material 40 expands, anchoring the plug material 40 to the artery wall 15, whereby the plug material 40 forms an occluding plug in the artery lumen 25 blocking or reducing blood flow therethrough (FIG. 1E). Expansion of the plug material 40 in the artery lumen 25 and in the extraarterial space 35 imparts radial forces acting upon surrounding tissues so as to contribute to the anchoring of the expandable plug material 40 to the artery wall 15.

The expandable plug material includes a porous natural or synthetic hydrogel material capable of expanding in a fluid environment so as to occlude a body vessel and become anchored thereto. The expandable plug material can be formed from expandable sponge-like material, expandable foam material, expandable ECM plug material, expandable polymeric material, expandable hydrogel material, or combination thereof.

The expandable plug material may be configured in the form of a solid material, or as a semi-gel material or flowable material configured to solidify and become anchored to the vessel wall when introduced into a bodily vessel under physiological temperature conditions.

In a desired embodiment, the expandable plug material includes a dried, compressed expandable ECM plug material. For example, the ECM plug material may be configured as a solid or semi-gel material, including dried, compressed ECM material. More particularly, the ECM material may be formed by treating an ECM tissue source material with a sufficient quantity of alkaline medium for a sufficient period of time to produce an ECM material expandable in an aqueous fluid environment by a factor of at least 2-fold, up to about 6-fold or more, including a capacity to absorb at least 10 times its weight in deionized water in forming a swollen collagenous hydrogel. The expandable ECM may be further characterized by a tensile strength of less than 50% relative to a corresponding non-expandable ECM material from which it was derived.

When deployed, the expandable biocompatible materials will be highly compacted to form an expandable plug material that is configured for passage through a hollow needle. Desirably, the expandable plug material will be in the form of dried, compacted material, having sufficient rigidity, resiliency, and size to be deployable through the hollow longitudinal bore of a needle having a size between about 13 Gauge to about 31 Gauge (external diameters between about 0.095 inches to about 0.010 inches, with internal diameters between about 0.077 inches and about 0.006 inches, respectively). An illustrative length for the vascular plug material may be less than about 100 mm, typically in the range of about 30 mm to about 50 mm. These diameters and lengths may of course be varied depending on the size of the needle's longitudinal bore and the size of the target vessel for occlusion.

An expandable plug material according to the present invention will be expandable when wetted, so as to achieve an expandable configuration. In one embodiment, the expandable plug material exhibits a capacity to expand at least 100% by volume, more preferably at least about 200% by volume, and typically in the range of about 300% by volume to about 1000% by volume, when wetted to saturation with deionized water. An expandable plug material for use in the present invention will also exhibit advantageous rates of expansion, achieving volume expansions as noted above in less than about 10 seconds, more preferably less than about 5 seconds, when immersed in deionized water.

The expandable sizes typical for the expandable plug materials of the present invention include diameters configured for expansion so as to occlude a body vessel having a cross-sectional diameter between about 1 mm to about 10 mm, and up to about 20 mm. The methods disclosed herein may be applied to occlusion of a variety of vessels or arteries, including those supplying tumors, neoplastic tissues, as well as other vessels where embolization (or occlusion) is required, as further described below.

The expandable biocompatible plug materials may be delivered using any suitable percutaneous needle device configured to penetrate vessel walls and to accommodate passage of expandable biocompatible materials therethrough. Typically, the expandable plug materials will be configured to allow delivery through a hollow needle having a size in a range between about 13 Gauge to about 31 Gauge (internal diameters of about 0.077 inches to about 0.006 inches, respectively). In a desired embodiment, the needle has a curved or laterally deflecting configuration. Exemplary needles and needle assemblies include various commercially available transseptal needles including the Ross Modified Transseptal needle (Cook Medical, Bloomington, Ind.), Brockenbrough Curved needle (Medtronic), or TSX Transseptal needle (C.R. Bard, Murray Hill, N.J.) in conjunction with an appropriate introducer sheath; as well as various transseptal needles, biopsy needles, or assemblies thereof described in U.S. Pat. Nos. 4,578,061, 5,190,528, 5,354,279, 5,464,395, 5,718,237, 6,217,554, 6,602,241, and 6,860,867, the disclosures of which are incorporated by reference herein.

The expandable plug material may be pushed through the needle through the application of pressure from a suitable pressure source; pusher member, such as a wire guide pusher; or any other suitable material displacement means known to those of skill in the art.

In desired embodiments, the anchored plug materials may be used to occlude vessels commonly or otherwise treated with embolization coils or embolic agents Accordingly, vessels may be targeted for occlusion for treating various liver or kidney tumors; breast tumors; skin, head, or neck tumors; tumors of the uterus or fallopian tubes; benign fibroid tumors; cerebral and intracranial aneurysms; arteriovenous malformation of the pelvis, kidney, liver, spine and brain; trauma; conditions of excessive bleeding; endometriosis, and the like.

In a preferred embodiment, a method for occluding a vessel is directed to an artery, especially an artery supplying blood to neoplastic tissues or tumors (both cancerous and non-cancerous, or benign). Exemplary arteries for occlusion include liver arteries, including but not limited to the hepatic and iliac arteries for liver tumors; renal arteries for kidney tumors; mammary arteries for breast cancers; pulmonary arteries for lung cancers; uterine arteries for fibroid tumors; or any other artery otherwise supplying blood to neoplastic tissues or tumors as known to those of skill in the art. The vessel may also be a vein for occlusion in patients with chronic venous insufficiency, superficial varicose veins in the leg, as well as other veins and indications therefore known to those skilled in the art.

The method for occluding vessels or arteries according to the present invention may provide an alternative or supplement to the use of embolization coils or other embolic agents for use in reducing blood flow to tumors or other tissues where embolization (or occlusion) is desired.

A highly compact plug material may be prepared by first hydrating or otherwise wetting a porous biocompatible material matrix, and then compressing and drying the element. Such preparative processes generally provide a denser, more rigid and stably compressed matrix than processes such as simple compaction of the dry matrix. Drying will be conducted sufficiently to stabilize the matrix. Drying of the compacted plug material may involve lyophilization (or freeze drying) or vacuum drying at ambient or elevated temperatures.

As a result, the drying procedure can reduce the liquid (e.g. water) content of the matrix to less than about 20% by weight, more preferably less than about 10% by weight. Compression forces can be applied so as to achieve a final density and/or configuration desired, and can be applied in one, two or three dimensions, including radially. For example, an expandable plug material will have a generally cylindrical shape with a generally circular cross section, and can have a diameter approximating that or smaller than that of catheter sheath through which it is to be passed.

When processed in this fashion, upon removal of the compaction force, the plug material is stabilized structurally and remains in its highly dense and compacted state until contacted with a liquid susceptible to absorption by the matrix, for example body fluids. The pores of the matrix are thereby stably retained at a volume substantially reduced from their maximum volume, but return to a partially or fully expandable state when the matrix material is wetted.

The expandable biocompatible materials may be formulated in a number of different ways. In one embodiment, one or more hydrated sheet(s) of expandable biocompatible material may be rolled and subsequently pressed and dried to form a porous matrix comprising a substantially unitary plug of dried expandable biocompatible material.

In another embodiment, the expandable biocompatible material may be applied to a mold or cast comprising to form a molded, or more specifically, a cylindrical-shaped plug. For example, a flowable, wet preparation of expandable biocompatible material may be applied to a mold or cast, whereby the cast preparation is lyophilized to form a shaped plug. In another embodiment, a cast for the plug may be prepared by casting a flowable, wet preparation of expandable ECM material against a biocompatible material sheet to form a wet composite, and drying the wet composite to form a dried composite.

Plug materials may be formed individually by compaction/drying of an appropriately sized plug element, or they may be individually excised from a larger compacted/dried plug.

Alternatively, the expandable plug material may be formed in situ from a flowable expandable ECM composition in a semi-gelled state. The flowable composition may include a comminuted expandable ECM composition comprising ECM particles in a suitable size and in an amount sufficient for retaining an injectable character facilitating injection through a needle. Further, composition may be formulated as a partially gelled flowable expandable ECM particle composition at lower (e.g. room) temperatures that can form a solid composition following injection into a patient under physiological temperature (about 37° C.).

The expandable biocompatible materials, including the expandable ECM materials may include one or more radiopaque markers or radiopaque coatings to assist in visualization of the material during a non-invasive procedure. For example, radiopaque substances containing tantalum, barium, iodine, or bismuth, e.g. in powder form, can be coated upon or incorporated within an ECM material or other biocompatible material during processing. The radiopaque substances may be incorporated homogeneously or inhomogeneously within or on the biomaterial to be implanted. For example, when the expandable ECM plug material is formed from one or more sheet(s), the radiopaque substance(s) can be spread along the surface of the layers. Alternatively, when the expandable biocompatible plug material is provided as a flowable composition, the radiopaque substance(s) can be combined in powdered form during preparation or to the hydrated/rehydrated expandable material prior to lyophilization. The radiopaque materials can be incorporated into the ECM- or biocompatible materials by a variety of common methods, such as adhesive bonding, lamination between two material layers, vapor deposition, and the materials and methods described in U.S. 2003/0206860, the disclosure of which is incorporated herein by reference.

Expandable ECM Plug Materials

In a desired embodiment, the expandable plug material includes an expandable ECM material formed by controlled contact with an alkaline substance as described below. In addition, chemical crosslinks may be introduced in the ECM material in an amount sufficient to produce a desired level of resiliency. The introduction of collagen crosslinks, for example with chemical crosslinkers such as glutaraldehyde, carbodimides, or other chemical crosslinkers identified herein, can enhance the resiliency of the foam plugs, and produce ECM materials sufficiently compressed for delivery through a needle. Increased resiliency in turn provides additional compression upon adjacent tissues when the compressed ECM materials are delivered to a body vessel and then allowed to expand in situ in a patient at a site at which occlusion is desired.

Notably, such treatments can be used to promote substantial expansion of the ECM material to form an effective occluding plug. The expandable ECM materials for use in the present invention may expand by at least about 2, at least about 3, at least about 4, at least about 5, at least about 6, and up to about 10 times its original bulk volume, or more. The magnitude of expansion can be regulated by varying the concentration of the alkaline substance, the exposure time of the alkaline substance to the material, and temperature, among others. These factors can be varied to achieve a material having the desired level of expansion, given the disclosures set forth below.

1. Alkaline Treatment

The application of alkaline substances to a source of native ECM material, as for example, a collagenous animal tissue layer, alters its structural morphology. ECM materials are composed of collagen fibrils comprising a quarter-staggered array of tropocollagen molecules formed as a triple helix of comprising three polypeptide chains linked together by covalent intramolecular bonds and hydrogen bonds. Additionally, covalent intermolecular bonds are formed between different tropocollagen molecules within the collagen fibril. Frequently, multiple collagen fibrils assemble with one another to form collagen fibers. It is believed that the addition of an alkaline substance to the material as described herein will not significantly disrupt the intramolecular and intermolecular bonds, but will denature the material so as to provide a processed thickness to an intact collagenous sheet material that is substantially greater (i.e. at least about 20% greater) than, and preferably at least twice the naturally-occurring thickness of, the collagenous animal tissue layer. Microscopic analysis (at 100× magnification) has established that non-expandable ECM materials exhibit a tightly bound collagenous network whereas the same views of an expandable material exhibit a denatured, but still intact, collagenous network reflecting expansion of the material.

The dried and compressed expandable ECM material for delivery is generally formed from an ECM source material treated with a sufficient quantity of alkaline medium for a sufficient period of time to produce an ECM material expandable in an aqueous fluid environment by a factor of at least 2-fold, up to about 6-fold or more, and to have a tensile strength of less than 50% of that of its corresponding non-expandable ECM material.

In addition to allowing for expansion of an ECM material, the application of an alkaline substance alters the collagen packing characteristics of the material as well. Altering such characteristics of the material can be caused, at least in part, by the disruption of the tightly bound collagenous network. A non-expandable ECM material having a tightly bound collagenous network typically has a continuous surface that is substantially uniform even when viewed under magnification (e.g. 100× magnification). Conversely, an expandable ECM material typically has a surface—that is quite different in that the surface is typically not continuous but rather presents collagen strands or bundles in many regions that are separated by substantial gaps in material between the strands or bundles. Consequently, an expandable ECM material typically appears more porous than a non-expandable ECM material. Moreover, the expandable ECM material can be demonstrated as having increased porosity, e.g. by measuring its permeability to water or other fluid passage.

With respect to the alkaline substance used to prepare an expandable ECM material, any suitable alkaline substance generally known in the art can be used. Suitable alkaline substances can include, for example, salts or other compounds that that provide hydroxide ions in an aqueous medium. Preferably, the alkaline substance comprises sodium hydroxide (NaOH). The concentration of the alkaline substance that is added to the material can be in the range of about 0.5 to about 4 M. Preferably, the concentration of the alkaline substance is in the range of about 1 to about 3 M. Additionally, the pH of the alkaline substance will typically range from about 8 to about 14. In preferred embodiments, the alkaline substance will have a pH of from about 10 to about 14, and most preferably of from about 12 to about 14.

In addition to concentration and pH, other factors such as temperature and exposure time will contribute to the extent of expansion. In this respect, it is preferred that the exposure of the ECM material to the alkaline substance is performed at a temperature of about 4 to about 45° C. In preferred embodiments, the exposure is performed at a temperature of about 25 to about 37° C., with 37° C. being most preferred. Moreover, the exposure time can range from about several minutes to about 5 hours or more. In preferred embodiments, the exposure time is about 1 to about 2 hours. In a particularly preferred embodiment, the ECM material is exposed to a 3 M solution of NaOH having a pH of 14 at a temperature of about 37° C. for about 1.5 to 2 hours. Such treatment results in the expansion of an ECM material to at least about twice its original volume. As indicated above, these processing steps can be modified to achieve the desired level of expansion.

Expandable ECM materials may be comminuted by shearing the material with a rotating blade, e.g. in a blender. For these purposes, it has been discovered that when utilizing an ECM material harvested as a decellurized sheet, the sheet can be contacted with the alkaline medium under conditions sufficient to substantially reduce the tensile strength of the sheet, so that the sheet material is disrupted by the rotating blade. Without sufficient reduction of tensile strength by the alkaline medium, the sheet material can tend to wrap around the rotating blade, thus frustrating the process of comminution. Therefore, prior to comminution by the blade or otherwise, the sheet may be desirably treated with the alkaline medium for a time and under conditions sufficient to reduce the tensile strength of the sheet to less than about 50% of its original tensile strength, more preferably to less than about 30% of its original tensile strength. Such methods can be practiced, for example, with harvested sheet-form ECM materials such as submucosa-containing sheets, e.g. obtained from small intestinal, stomach or bladder tissue, pericardial tissue, peritoneal tissue, fascia, dermal tissue, and other sheet-form ECM materials.

2. Crosslinking Treatment

With regard to compressible/expandable plug materials described herein, cross-linking and/or expansion additives can be used to impart desirable compression/re-expansion properties. For example, crosslinking of compressed ECM materials can promote re-expansion of the construct after implantation into a patient.

An expandable ECM material can be crosslinked either before or after it is formed into a medical device, or both. Increasing the amount (or number) of crosslinkages within the material or between two or more layers of the material can be used to enhance its strength. However, when a remodelable material is used, the introduction of crosslinkages within the material may also affect its resorbability or remodelability. Consequently, in certain embodiments, an ECM material will substantially retain its native level of crosslinking, or the amount of added crosslinkages within the medical device will be judiciously selected depending upon the desired treatment regime. In many cases, the material will exhibit remodelable properties such that the remodeling process occurs over the course of several days or several weeks. In certain preferred embodiments, the remodeling process occurs within a matter of about 5 days to about 12 weeks.

Crosslinking of the expandable ECM material may be achieved by photo-crosslinking techniques, or by the application of a crosslinking agent, such as by chemical crosslinkers, or by protein crosslinking induced by dehydration or other means. Chemical crosslinkers that may be used include for example aldehydes such as glutaraldehydes, diimides such as carbodiimides, e.g., 1-ethyl-3-(3-dimethylaminopropyl)carbodiimide hydrochloride (EDC), diisocyanates such as hexamethylene-diisocyanate, ribose or other sugars, acylazide, sulfo-N-hydroxysuccinamide, or polyepoxide compounds, including for example polyglycidyl ethers such as ethylene glycol diglycidyl ether, available under the trade name DENACOL EX810 from Nagese Chemical Co., Osaka, Japan, and glycerol polyglycerol ether available under the trade name DENACOL EX 313 also from Nagese Chemical Co. Typically, when used, polyglycerol ethers or other polyepoxide compounds will have from 2 to about 10 epoxide groups per molecule.

3. Additives

In addition to the alkaline treatment and crosslinking, one or more additives may be incorporated into the expandable ECM material to help promote expansion of the material once implanted into a patient. For example, a sponge-like expandable ECM material including one or more additives can be compressed and placed into a delivery device. Compression of the material allows the material to be more easily transferred through a catheter to a patient. Upon delivery, the material can expand to at least about its original size prior to compression. Such additives can be included in the ECM material to expand the material at a faster rate than would otherwise be achievable in the absence of the one or more additives. These additives may be applied to the expandable ECM material as a premanufactured step, immediately prior to the procedure (e.g. by soaking the material in a solution containing the additive(s)), or during or after engraftment of the material in the patient.

4. Lyophilization

The expandable ECM materials for use in the present invention may be freeze-dried by lyophilization. Freezing can be done at a temperature of about $-80°$ C. for about 1 to about 4 hours; and lyophilization can be performed for about 8 to about 48 hours. In addition, the expandable ECM materials may be comminuted prior to lyophilization.

In preferred forms, the expandable ECM materials are capable of volumetric compression when dry at a ratio of at least 10:1 (i.e. the compressed form occupies no more than 10% of its original, relaxed and unexpanded volume), more preferably at a ratio of at least 20:1. At the same time, in preferred forms, the compressed constructs are capable of re-expansion to substantially their original volume (e.g. at least about 80% of their original volume, more preferably at least 90%, and most preferably at least 95%) within about 30 seconds when delivered in their dry, compressed form into a volume of water.

5. ECM Material Forms

The expandable ECM source materials for the present invention can be provided in a variety of forms during the processing of ECM materials for use in the present invention. These forms include solid plugs, cast bodies, flowable compositions (e.g., a fluidized aqueous composition), gels, sponges, foams, and sheet materials as further described herein.

The expandable plug material for occluding a body vessel may be formulated to provide an expandable diameter between about 1 mm to about 10 mm, and up to about 20 mm.

In addition, an expandable ECM material may be formed into a sponge-like or foam construct for implantation into a patient. Preferably, a sponge-like construct will be constructed such that the material does not fully expand until after delivery to a desired site. In these instances, an expandable ECM material can be encapsulated, either partially or wholly, so as to prevent the premature expansion of the material until it reaches its intended delivery site. For example, a dried sponge-like material as described herein can be compressed and either partially or wholly encapsulated into a biodegradable capsule. In such embodiments, the capsule can retain the material in a compressed state so as to prevent the premature expansion of the expandable ECM material during delivery. This allows the material to be delivered to a desired location before full expansion occurs. Biocompatible materials suitable for use in forming a biodegradable capsule are generally known in the art and can include, for example, gelatin.

In another embodiment, the expandable ECM material may be processed into a flowable composition, for instance using techniques as described in U.S. Pat. No. 5,275,826. In this regard, solutions or suspensions of the expandable ECM material can be prepared by comminuting and/or digesting the material with a protease (e.g. trypsin or pepsin), for a period of time sufficient to solubilize the material and form a substantially homogeneous solution.

Expandable ECM materials may be comminuted by, tearing, cutting, grinding, shearing (e.g. combined with a liquid and sheared in a blender), or the like. The expandable ECM material typically has a spongy and porous structure, so these techniques may not be needed to the extent they would be needed to solubilize a non-expandable ECM material. Grinding the material in a frozen or freeze-dried state is advantageous, although good results can be obtained as well by subjecting a suspension of pieces of the material to treatment in a high speed blender and dewatering, if necessary, by centrifuging and decanting excess waste. The comminuted material can be dried, for example freeze dried, to form a particle composition or particulate comprising a plurality of ECM particles of substantially the same or differing sizes. The particulate can be hydrated with water or buffered saline and optionally other pharmaceutically acceptable excipients, to form a fluidized, expandable ECM material, e.g. having a viscosity of about 2 to about 300,000 cps at $25°$ C. Higher viscosity compositions can have a gel or paste consistency. A fluidized composition prepared from an expandable ECM material can be dried to form a sponge-like solid or foam material. Thus, dry sponge or foam form materials for use in the present invention may be prepared by drying expandable ECM material gels.

6. ECM Source Materials

The expandable ECM materials of the present invention may be derived from native ECM tissue source materials and/or tissue extracts therefrom as described below. Suitable ECM tissue source materials may be isolated from warm-blooded vertebrate, especially mammals, and may be processed so as to have remodelable properties promoting cellular invasion and ingrowth, as well as biotropic properties promoting angiogenesis, for example. Exemplary ECM tissue source materials include submucosa, renal capsule membrane, dermal collagen, dura mater, pericardium, fascia lata, serosa, and peritoneum or basement membrane layers, including liver basement membrane. Suitable submucosa materials for these purposes include, for instance, intestinal submucosa, including small intestinal submucosa, stomach submucosa, urinary bladder submucosa, and uterine submucosa. These and other similar animal-derived tissue layers can be purified, expanded, and processed as previously described in U.S. Pat. No. 6,206,931 to Cook et al., the disclosures of which are incorporated by reference herein.

7. ECM Sheet Material Processing

Expandable ECM materials for use in the present invention may be processed from expandable ECM sheet materials or from non-expandable ECM sheet materials treated as described above to form expandable ECM sheet materials. Generally, the ECM sheet materials will have a thickness in the range of about 0.2 mm to about 2 mm, more preferably about 0.4 mm to about 1.5 mm, and most preferably about 0.5 mm to about 1 mm. If necessary or desired, a multilaminate material can be used. For example, a plurality of (i.e. two or more) layers of an expandable ECM material can be bonded or otherwise coupled together to form a multilaminate structure. Illustratively, two, three, four, five, six, seven, or eight or more layers of an expandable ECM material can be bonded together to provide a multilaminate material. In certain embodiments, two to six expandable, submucosa-containing layers isolated from intestinal tissue of a warm-blooded vertebrate, particularly small intestinal tissue, are bonded together to provide a medical material. Porcine-derived small intestinal tissue is preferred for this purpose. In alternative embodiments, one or more sheets of a non-expandable collagenous material (e.g., submucosa) can be bonded or otherwise coupled to one or more sheets of an expandable ECM material. Any number of layers can be used for this purpose and can be arranged in any suitable fashion with any number of layers of a non-expandable ECM material bonded to any number of layers of an expandable ECM material. The layers of collagenous tissue can be bonded together in any suitable fashion, including dehydrothermal bonding under heated, non-heated or lyophilization conditions, using adhesives as described herein, glues or other bonding agents, crosslinking with chemical agents or radiation (including UV radiation), or any combination of these with each other or other suitable methods.

A variety of dehydration-induced bonding methods can be used to fuse portions of multi-layered medical materials together. In one preferred embodiment, the multiple layers of material are compressed under dehydrating conditions. The term "dehydrating conditions" can include any mechanical or environmental condition which promotes or induces the removal of water from the multi-layered medical material. To promote dehydration of the compressed material, at least one of the two surfaces compressing the matrix structure can be water permeable. Dehydration of the material can optionally be further enhanced by applying blotting material, heating the matrix structure or blowing air, or other inert gas, across the exterior of the compressing surfaces. One particularly useful method of dehydration bonding multi-layered medical materials is lyophilization, e.g. freeze-drying or evaporative cooling conditions.

Another method of dehydration bonding comprises pulling a vacuum on the assembly while simultaneously pressing the assembly together. This method is known as vacuum pressing. During vacuum pressing, dehydration of the multi-layered medical materials in forced contact with one another effectively bonds the materials to one another, even in the absence of other agents for achieving a bond, although such agents can be used while also taking advantage at least in part of the dehydration-induced bonding. With sufficient compression and dehydration, the multi-layered medical materials can be caused to form a generally unitary laminate structure.

It is advantageous in some aspects of the invention to perform drying operations under relatively mild temperature exposure conditions that minimize deleterious effects upon the multi-layered medical materials of the invention, for example native collagen structures and potentially bioactive substances present. Thus, drying operations conducted with no or substantially no duration of exposure to temperatures above human body temperature or slightly higher, say, no higher than about 38° C., will preferably be used in some forms of the present invention. These include, for example, vacuum pressing operations at less than about 38° C., forced air drying at less than about 38° C., or either of these processes with no active heating at about room temperature (about 25° C.) or with cooling. Relatively low temperature conditions also, of course, include lyophilization conditions. It will be understood that the above-described means for coupling two or more multi-layered medical materials together to form a laminate can also apply for coupling together one or more layers of peritoneum and fascia when these layers are isolated independent from one another.

When a multi-layered laminate material is contemplated, the layers of the laminate can be additionally crosslinked to bond multiple layers of a multi-layered medical material to one another. Crosslinking of multi-layered medical materials can also be catalyzed by exposing the matrix to UV radiation, by treating the collagen-based matrix with enzymes such as transglutaminase and lysyl oxidase, and by photocrosslinking. Thus, additional crosslinking may be added to individual layers prior to coupling to one another, during coupling to one another; and/or after coupling to one another.

A non-expandable source material for preparing an expandable ECM material may include a variety of bioactive components including, for example, growth factors, glycoproteins, glycosaminoglycans, proteoglycans, nucleic acids, and lipids. Under certain circumstances, treating the material with an alkaline substance under conditions as described herein may significantly reduce, if not completely eliminate, the bioactivity of these components from the material. Indeed, the treatment of the ECM material with an alkaline substance can result in an ECM material which is substantially devoid of growth factors, glycoproteins, glycosaminoglycans, proteoglycans, nucleic acids, and lipids. Accordingly, the treatment of an ECM material with an alkaline substance as described herein can cause the material to expand to at least about twice its original volume, can alter the surface and/or porosity characteristics of the material, and can deplete the material of certain bioactive components.

In some embodiments, an ECM sheet of ECM material may be treated with the alkaline medium so as to expand it as described herein, while retaining an amount of a growth factor such as FGF-2, or another bioactive component such as fibronectin and/or heparin, that is/are native to the source tissue for the ECM- or other collagenous materials.

8. Incorporation of Bioactive Components and Bioactive Agents

In other embodiments, selected bioactive components that were previously removed from the ECM material can be returned to the material. For example, the present invention can provide an expandable ECM material, which is substantially devoid of nucleic acids and lipids, but which has been replenished with one or more growth factors, glycoproteins, glycosaminoglycans, or proteoglycans or combinations thereof. These bioactive components can be returned to the material by any suitable method. For instance, in certain forms, a tissue extract containing these components can be prepared and applied to an expandable ECM material. In one embodiment, the expandable ECM material may be incubated in a tissue extract for a sufficient time to allow the bioactive components contained therein to associate with the expandable ECM material. The tissue extract may, for example, be obtained from non-expandable ECM tissue of the same type used to prepare the expandable material. Other means for returning or providing bioactive components to an expandable ECM material include spraying, impregnating, dipping, etc. as known in the art.

By way of example, an expandable ECM material may be modified by the addition of one or more growth factors such as basic fibroblast growth factor (FGF-2), transforming growth factor beta (TGF beta), epidermal growth factor (EGF), platelet derived growth factor (PDGF), and/or cartilage derived growth factor (CDGF). These growth factors may be prepared from cell or tissue extracts, or they may be synthetically produced by recombinant technology. As well, an expandable ECM material may be replenished with other biological components such as heparin, heparin sulfate, hyaluronic acid, fibronectin and the like. Thus, generally speaking, an expandable ECM material may include a bioactive component that induces, directly or indirectly, a cellular response such as a change in cell morphology, proliferation, growth, protein, or gene expression. The preparation of submucosa extracts is described in, for example, U.S. Pat. No. 6,375,989.

In addition to, or as an alternative to the inclusion of native bioactive components, such as those provided in a submucosa or other ECM extract, non-native bioactive components including those synthetically produced by recombinant technology or other methods, may be incorporated into the expandable ECM material. These non-native bioactive components may be naturally-derived or recombinantly produced proteins that correspond to those natively occurring in the ECM tissue, but perhaps of a different species (e.g. human proteins applied to collagenous ECMs from other animals, such as pigs).

In addition, bioactive agents may be incorporated into the expandable ECM materials. Bioactive agents for use in the present invention may include, for example, any agent capable of promoting occlusion or stable engraftment of the plug material into the body vessel tissue. The bioactive agent may be an organic compound, inorganic compound, synthetic molecule, drug, antiproliferative agent, paclitxel, synthetic polymer, antibiotic, biological polymer, peptide, peptidomimetic, polypeptide, growth factor, antibody, peptide conjugate, nucleic acid, oligonucleotide, polynucleotide, ribozyme, or small interfering RNA (siRNA).

In addition, the bioactive agent may have one or more beneficial properties having thrombogenic, fibrogenic, angiogenic, antiproliferative, bactericidal, wound healing, fibroblast stimulatory, vascularization promoting, cell and/or tissue attachment promoting, bioremodeling, blood clotting, ECM-promoting agents including, for example, antibiotics, thrombin, fibrinogen, and the like.

As with the bioactive components previously described, these substances may be applied to the expandable ECM material as a premanufactured step, immediately prior to the procedure (e.g. by soaking the material in a solution containing a suitable antibiotic such as cefazolin), or during or after engraftment of the material in the patient.

Additional expandable and non-expandable ECM compositions, including their use in making the expandable plug materials for use in the present invention are described in U.S. patent application Ser. No. 12/488,996, entitled "Composite Extracellular Matrix Materials and Medical Products Formed Therefrom," filed Jun. 22, 2009, and U.S. patent application Ser. No. 12/488,974, entitled "Compressible/Expandable Medical Graft Products, and Methods for Applying Hemostasis," filed Jun. 22, 2009, the disclosures of which are expressly incorporated by reference herein.

Other Expandable Biocompatible Occluding Materials

Other expandable biocompatible occluding materials of the present invention include virtually any natural or synthetic porous, hydrophilic hydrogel material known to those of skill in the art which can be formed into a compressed cylinder or tube capable of expanding in a fluid environment so as to occlude a body vessel. This may include a variety of non-native occluding materials or native occluding materials, including purified collagen-based materials, which fail to maintain an ECM configuration. Exemplary expandable occluding materials that can be formed into a suitably compressed hydrogel material, sponge-like body, or foam body, include a variety of natural or synthetic polymeric materials, fibrous materials; and combinations thereof.

Examples of natural polymers that expand in the presence of aqueous fluids such as biological fluids to form hydrogels, include a variety of natural polymers, including but are not limited to collagens, hydrolyzed collagens (gelatin), collagen sponges and plugs, COLLASTAT® Hemostatic Sponge (Vitaphore Corp.), VITACOL™ (Vitaphore Corp.), fibronectin, fibrin, albumin, crosslinked derivatives therefrom, and the like. Other examples of water-swelling polymers include polysaccharides, mucopolysaccharides, cyclodextrins, hyaluronates, pectins, agarose, alginate, chitosan, chitosan derivatives, including chitosan modified with fructose or galactose; and the like.

Hydrogels, foams, or sponges may also be formed from a variety of synthetic polymers, copolymers, and block copolymers, including non-biodegradable polymers, biodegradable polymers, and cross-linked derivatives therefrom. These polymeric materials may be configured to expand in the presence of aqueous fluids such as biological fluids, and may be cross-linked with agents, such as ethylene glycol dimethacrylate or methylene-bis-acrylamide.

Exemplary synthetic polymers include polyurethanes, including THORALON™ (THORATEC, Pleasanton, Calif.), as described in U.S. Pat. Nos. 4,675,361, 6,939,377, and U.S. Patent Application Publication No. 2006/0052816, the disclosures of which are incorporated by reference herein; acrylates, including but not limited to poly(hydroxyalkyl methylacrylates), such as poly(hydroxyethyl methacrylate), poly(glyceryl methacrylate)poly(acrylamide), and poly(vinyl alcohol)poly(ethylene glycol) diacrylate; and various silicones.

Exemplary non-biodegradable polymers include but are not limited to poly(hydroxyalkyl methylacrylates), including poly(glyceryl methacrylate)poly(acrylamide), poly(methacrylamide) and derivatives; fluoropolymers, including but not limited to homopolymers of polytetrafluoroethylene and copolymers of polytetrafluoroethylene in which the co-monomer is ethylene, chlorotrifluoroethylene, perfluoroalkoxytetrafluoroethylene, and fluorinated propylene; polyolefins, including but not limited to polypropylene, polyethylene, polyethylene terephthalate, expandable polytetrafluoroethylene (ePTFE), DACRON®, polystyrene, and ultra high molecular weight polyethylene; polyethers, including but not limited to poly(ethylene oxide); water-soluble polymers, including but not limited to poly(vinyl alcohol), polyvinylpyrrolidone, and poly(hydroxyethyl methacrylate; carboxy alkyl celluloses, including but not limited to carboxymethyl cellulose; partially oxidized cellulose, cross-linked derivatives therefrom; and other synthetic polymers known to those of skill in the art.

Exemplary biodegradable polymers include polyphosphazenes, polyphosphoesters, polyanhydrides, polyethylene oxides, polyethylene oxide-co-polypropyleneoxide block copolymers, polylactides, polyglycolide, polycaprolactone, poly(3-hydroxy-butyric acid), polyvinyl alcohols, PEG, dextran, alginic acid and sodium alginate.

Expandable plug materials, including hydrogel, foam, sponge, and associated materials therefrom, as well as methods for molding or machining such materials into a plug or tube are further described in U.S. Patent Application Numbers 2006/0008419, 2005/0085885, and 2003/0109899; and U.S. Pat. Nos. 6,818,018; 6,602,261; 6,238,403; 6,245,090; 5,823,198; 5,570,585; 5,456,693; 5,258,042; and 4,663,358, the disclosures of which are incorporated by reference herein.

In addition, fibrous materials may be incorporated into the expandable biocompatible materials to provide increased thrombogenicity. Exemplary thrombogenic fibrous materials and threads include, but are not limited to, DACRON®, cotton, silk, wool, polyester thread and the like.

Further, non-native bioactive components and bioactive agents, as described above may be similarly incorporated into these expandable biocompatible materials.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A method for occluding an artery in a patient to block or reduce blood flow to a neoplastic tissue or tumor comprising:
   a. puncturing an artery wall in an artery of a patient at a proximal artery entry site;
   b. extending a hollow needle through the proximal entry site into the artery lumen;
   c. extending the needle through the artery lumen;
   d. puncturing the artery wall at a distal artery exit site;
   e. ejecting an expandable biocompatible plug material through the distal end of the needle into the extravascular space surrounding the distal artery exit site;
   f. continuing to eject the expandable biocompatible plug material while retracting the needle back though the distal artery exit site into the artery lumen;
   g. continuing to eject the expandable biocompatible plug material in the artery lumen, such that the plug material continuously extends between the extravascular space surrounding the distal artery exit site into the artery lumen;
   h. allowing the plug material to expand in the extravascular space, in the distal artery exit site, and in the artery lumen, anchoring the plug material to the artery wall, wherein the patient has a neoplastic condition, and wherein expansion of the plug material forms an occluding plug in the artery lumen blocking or reducing blood flow between the artery and a neoplastic tissue or tumor in the patient.

2. The method of claim 1, wherein the artery is a hepatic artery, renal artery, mammary artery, uterine artery, or pulmonary artery.

3. The method of claim 1, wherein the expandable biocompatible plug material is selected from the group consisting of expandable sponge material, expandable foam material, expandable ECM plug material, expandable polymeric material, expandable hydrogel material, or combination thereof.

4. The method of claim 3, wherein the expandable biocompatible plug material comprises expandable ECM plug material.

5. The method of claim 4, wherein the expandable ECM plug material is configured as a solid plug.

6. The method of claim 4, wherein the expandable ECM plug material comprises dried, compressed material.

7. The method of claim 4, wherein the expandable ECM plug material is expandable by a factor of at least two-fold.

8. The method of claim 4, further comprising the step of forming treating an ECM tissue source material with a sufficient quantity of alkaline medium for a sufficient period of time to produce an ECM material expandable in an aqueous fluid environment by a factor of at least 4-fold and exhibiting the capacity to absorb at least 10 times its weight in deionized water; and adding the ECM material to the biocompatible plug material.

9. The method of claim 4, wherein the expandable ECM plug material has a tensile strength of less than 50% relative to a corresponding non-expandable ECM material from which it was derived.

10. The method of claim 1, wherein the expandable biocompatible plug material is configured as a solid plug.

11. The method of claim 1, wherein the expandable biocompatible plug material is configured as a semi-gel composition or flowable composition.

12. The method of claim 1, wherein the step of puncturing the artery wall at a distal artery exit site is performed only once.

13. A method for occluding a blood vessel in a patient comprising:
   a. puncturing a blood vessel wall in a vessel at a proximal vessel entry site;
   b. extending a hollow needle through the proximal vessel entry site into the vessel lumen;
   c. extending the needle through the vessel lumen;
   d. puncturing the vessel wall at a distal vessel exit site;
   e. ejecting an expandable biocompatible plug material through the distal end of the needle into the extravascular space surrounding the distal vessel exit site;
   f. continuing to eject the expandable biocompatible plug material while retracting the needle back though the distal vessel exit site into the vessel lumen;
   g. continuing to eject the expandable biocompatible plug material in the vessel lumen, such that the plug material continuously extends between the extravascular space surrounding the distal vessel exit site into the vessel lumen;

h. allowing the plug material to expand in the extravascular space, in the distal vessel exit site, and in the vessel lumen, anchoring the plug material to the vessel wall, whereby the plug material forms an occluding plug in the vessel lumen blocking or reducing blood flow therethrough.

14. The method of claim 13, wherein the blood vessel is occluded to treat a disease or condition selected from the group consisting of cancer; cerebral or intracranial aneurysms; arteriovenous malformations of the pelvis, kidney, liver, spine or brain; and conditions of excessive bleeding.

15. The method of claim 13, wherein the step of puncturing the vessel wall at a distal vessel exit site is performed only once.

* * * * *